United States Patent

Engel et al.

[11] Patent Number: 5,976,550
[45] Date of Patent: Nov. 2, 1999

[54] DIETARY FOOD SUPPLEMENT

[76] Inventors: Peter H. Engel; Howard Cohl, both of 144 N. Robertson Blvd., Suite 103, Los Angeles, Calif. 90048-3102

[21] Appl. No.: 09/196,527

[22] Filed: Nov. 20, 1998

[51] Int. Cl.⁶ .................... A61K 35/78; A61K 39/385; A61K 31/73; A61K 31/205; A61K 31/19; A61K 31/045
[52] U.S. Cl. .................... 424/195.1; 514/55; 514/556; 514/557; 514/727; 514/909
[58] Field of Search ............... 424/195.1; 514/55, 514/556, 557, 727, 909

[56] References Cited

PUBLICATIONS

CA 128:114361, Ventura, 1996.
CA 128114362, Veneroni et al., 1996.
CA 129:117664, Okuda et al., 1998.
Fat Blocker Diet Book, Chapter 3; St. Martin's Press 1997, relevant pp. 35 and 36.

*Primary Examiner*—Kimberly Jordan
*Attorney, Agent, or Firm*—Fattibene & Fattibene; Arthur T. Fattibene; Paul A. Fattibene

[57] ABSTRACT

A dietary food supplement for weight reduction formed of a mixture of a sugar based confectionary containing therapeutic amounts of chitosan, kava and a fat burning nutriceutical which may include choline/inusital, chromium picolinate, beta-hydroxy-beta-methyl butyrate, L-carnitine and pyruvate or any combination thereof.

6 Claims, No Drawings

DIETARY FOOD SUPPLEMENT

FIELD OF THE INVENTION

This invention is directed to a dietary food supplement, and more specifically to a weight reducing sugar-based confectionary product containing chitosan together with a very mild anesthetic and a fat burning nutriceutical.

BACKGROUND OF THE INVENTION

It has been well documented that chitosan, when eaten within a half-hour before a meal, acts electrostatically to attract part of the fat that is consumed during a meal and carries it through the body. However effective chitosan may be in removing fat, it does not function as a deterrent to the amount of food or fat which one may ingest during a meal.

SUMMARY OF THE INVENTION

An object of this invention is to provide a dietary supplement which, in addition to chitosan, includes an appetite reducing substance such as a sugar-based confectionary and a mild anesthetic substance to mildly anesthetize the tongue and lips so as to make food both slightly less flavorable and less organaleptically desirable and so to deter one from ingesting more food than is necessary purely for dietary needs.

Another object is to provide a dietary food supplement containing chitosan and an appetite reducing substance together with a nutriceutical to burn or better metabolize whatever fat the body does consume.

Another object of this invention is to provide a dietary food supplement in the form of a sugar based or candy confectionary containing chitosan and a mild anesthetic to diminish one's desire for food and including a metabolizing nutriceutical to better metabolize any fat that is ingested.

The foregoing objects and other features and advantages are attained by formulating a dietary food supplement that comprises a sugar based or sugar-coated confectionary which is combined with chitosan, kava and a fat burning nutriceutical selected from the group consisting of chromium picolinate, HMB (beta-hydroxy-beta-methyl butyrate), L-carnitine, pyruvate, or a combination thereof.

DETAILED DESCRIPTION

The dietary food supplement embodying the invention includes a candy or sugar based confectionary in the form of a well-formulated health food bar. The preferred sugar based confectionary or candy bar is about one-quarter the size of a health food bar, or about a third of an ounce, i.e. about 10 grams. However, the size or weight of the sugar based confectionary is not especially critical.

Generally, most people suffer from a strange phenomenon in that they develop a sense of acute hunger when they are only slightly hungry. Such people feel ravenous and suffer from sharp hunger pangs even though the actual need for food is limited. This phenomenon is most easily observed when one orders a meal on an empty stomach at a restaurant, or worse at an all-you-can-eat buffet, only to realize he or she has ordered far more food than one can eat.

In this modern world, where food is generally in abundance, one tends to eat quickly and more; and before the hypothalamus has had time to react, which means that one will eat far more than the minor lack of food that was the initial cause of the hunger pangs.

The hypothalamus is a tiny organ near the front of the brain which, in the past, has been largely ignored. Now, it has been recognized as being a vastly important organ, and researchers have now realized that the hypothalamus has a determinal impact on how much serotonin the brain releases. It has been noted that serotonin quite literally controls the degree to which one feels hunger, as well as other emotions.

While the exact mechanism by which the hypothalamus releases serotonin to impact on one's hunger is not fully understood, it is believed that when one ingests food, the hypothalamus gradually takes note and causes the release of serotonin. The serotonin thus allows the activation of an electrical stimuli to inform the brain when one has eaten enough. The satiated signal thus formed causes one to stop eating.

With the abundance of available food, there is hardly any delay in satisfying hunger and thus one tends to overeat. The fact that a delay is required to allow the hypothalamus to wake up so as to generate the necessary serotonin to tell one to stop eating presents a problem in that one may well continue to eat believing they are still hungry, even though if one would have waited a few minutes, one would realize that he or she was not.

An effective way to overcome this problem is to "wake up" the hypothalamus in advance of each major meal by at least fifteen to twenty minutes. In this way, when the meal is actually being consumed, the hypothalamus has already generated part of the serotonin so that there is less time delay between being full and feeling full, and the electrical stimuli generated by the serotonin creates a satiating signal to cause one to stop eating.

In accordance with this invention, there is provided a dietary supplement comprising a piece of candy or a sugar based confectionary, e.g. a toffee or a hard candy formed with a soft center containing therapeutic amounts of chitosan, kava and a metabolizing nutriceutical selected from the group consisting of chromium picolinate, beta-hydroxy-beta-methyl burate (HMB), L-carnitine, and/or pyruvate or a combination thereof.

The candy or sugar based confectionary portion of the dietary supplement, when taken before a meal, has a natural tendency to reduce one's appetite.

Kava is a virtually tasteless, very mild skin anesthetic which is formed from the root of a shrubbery species of a southern Pacific pepper plant that has two important characteristics. The active ingredients in kava are chemicals known as kavalatones which act as a mild and harmless muscle relaxant and tranquilizer. They probably effect the hippocampus, i.e. the brain structure associated with emotions and feelings; slightly depressing it and thus function to reduce ordinary stress. It has been noted that kava has at least two incidental but very helpful effects. They both result in a tendency for people who ingest the product to regularly lose weight. When one is relaxed, content and unstressed, one has a tendency to eat less than those people who are under constant tension or stress.

The other effect of kava is that it has a mild anesthetic effect that slightly numbs the lips and the tip of the tongue, which is barely noticeable and imparts a generally pleasant sensation. This has a surprising behavioral effect of causing one to unconsciously reduce the amount one eats or drinks.

It has been observed that people often seek oral gratification by smoking, chewing gum, gnawing on the end of a pencil and the like. Often, many people eat and drink excessively, primarily for oral gratification, rather than to satisfy any real, physical hunger. It has been noted that this behavior pattern is minimized when one ingests kava. Apparently, the slight numbing effect attributed to the kava in the instant dietary supplement will lessen one's need to eat and drink in order to satisfy one's oral gratification. While one can taste and enjoy food, one is less prone to eat unless he or she is actually hungry.

By incorporating a therapeutic amount of kava in the sugar confectionary or candy portion of the instant dietary supplement requires chewing the same before each major meal. Such chewing allows the kava to stay in the mouth for a time sufficient to achieve the necessary numbing effect by the time the meal starts. As a result, one will eat only enough to satisfy his or her physiological need for food, and not likely to eat enough to satisfy his or her additional psychological needs.

The instant dietary supplement also includes therapeutic amounts of chitosan, which itself is an insoluble and inert fibrous matter of a chiton, an elongated bilaterally symmetrical marine mollusk, having a positive electrostatic charge. Fat which one consumes has a negative electrostatic change which means the fat is normally attracted to chitosan. As a result, when the instant dietary supplement containing chitosan is ingested prior to a major meal, the fat consumed during the meal is attracted to the chitosan. Instead of the fat being metabolized, it is attracted to the chitosan to form a non-digestible amalgam of chitosan and fat that passes through the intestines and out of the body. Thus, the presence of chitosan blocks the assimilation of fat by the body. Carefully controlled studies have established that for each gram of chitosan ingested by rats, they excreted 4 to 5 more grams of fat than the control group. Studies have shown that chitosan markedly increases the fecal lipid excretion and reduces the apparent fat digestibility to about half relative to the control group. In other words, by ingesting chitosan, one digests smaller amounts of fat as more of the fat exits the body together with the stool.

Included in the instant dietary supplement are therapeutic amounts of fat "burning" or metabolizing nutriceuticals or a combination thereof selected from the group consisting of chromium picolinate, beta-hydroxy-beta-methyl butyrate (HMB), L-carnitine and pyruvate. These nutriceuticals function to help burn whatever fat the body does consume.

The synergistic effect of the ingredients comprising the instant dietary supplement as described herein greatly increases the weight loss impact over that of simple chitosan. The fat blocking characteristic of chitosan is enhanced by the combination therewith of small amounts of a sugar based confectionary or candy that lowers the appetite by the pre-meal ingestion thereof, while the therapeutic amount of kava effects a reduction in one's desire to eat because of its anesthetic effect in the mouth. The indicated nutriceuticals ingredient mixed therein function to burn whatever fat the body has consumed, i.e. to metabolize better any fat that is ingested and not attracted to the chitosan.

While the present invention has been described with respect to a particular embodiment, modifications and variations may be made without departing from the spirit or scope of this invention.

What is claimed is:

1. A dietary food supplement to achieve a fat-reducing effect comprising:
   a sugar based confectionary,
   said sugar based confectionary having mixed therein therapeutic amounts of chitosan and kava.

2. A dietary food supplement as defined in claim 1 and comprising:
   a therapeutic amount of a nutriceutical to metabolize fat that is ingested.

3. A dietary food supplement as defined in claim 2 wherein said nutriceutical is selected from the group consisting of chromium picolinate, beta-hydroxy-beta-methyl butyrate, L-carnitine and pyruvate.

4. A composition of matter to achieve a fat reducing effect comprising:
   a sugar based confectionary to be eaten before a meal to minimize the appetite,
   a therapeutic amount of chitosan mixed in said confectionary together with a therapeutic amount of kava whereby said chitosan functions to attract fat to form a non-digestible amalgam of chitosan and fat that passes out of the body and whereby said kava functions to reduce a desire to eat by mildly anesthetizing the mouth,
   and a nutriceutical to metabolize any fat that is ingested and not passed through the body by the action of said chitosan.

5. A composition of matter to achieve a fat reducing effect as defined in claim 4 wherein said nutriceutical is selected from the group consisting of chromium picolinate, beta-hydroxy-beta-methyl butyrate, L-carnitine and pyruvate.

6. A composition of matter comprising of a mixture of a sugar based confectionary, chitosan and kava.

* * * * *